(12) United States Patent
Pilch et al.

(10) Patent No.: US 8,980,229 B2
(45) Date of Patent: Mar. 17, 2015

(54) DENTIFRICE COMPOSITIONS AND METHODS FOR TREATING AND PREVENTING DAMAGE TO TOOTH SURFACES

(75) Inventors: Shira Pilch, Highland Park, NJ (US); James Gerard Masters, Ringoes, NJ (US)

(73) Assignee: Colgate-Palmolive Company, New York, NY (US)

(*) Notice: Subject to any disclaimer, the term of this patent is extended or adjusted under 35 U.S.C. 154(b) by 11 days.

(21) Appl. No.: 13/262,003

(22) PCT Filed: Apr. 1, 2009

(86) PCT No.: PCT/US2009/039198
§ 371 (c)(1),
(2), (4) Date: Sep. 29, 2011

(87) PCT Pub. No.: WO2010/114540
PCT Pub. Date: Oct. 7, 2010

(65) Prior Publication Data
US 2012/0027696 A1 Feb. 2, 2012

(51) Int. Cl.
*A61Q 11/00* (2006.01)
*A61K 8/00* (2006.01)
*A61K 8/19* (2006.01)
*A61K 8/25* (2006.01)

(52) U.S. Cl.
CPC . *A61Q 11/00* (2013.01); *A61K 8/19* (2013.01); *A61K 8/25* (2013.01)
USPC .................. 424/49; 424/54; 424/724

(58) Field of Classification Search
USPC .......................................... 424/49
See application file for complete search history.

(56) References Cited

U.S. PATENT DOCUMENTS

| | | | |
|---|---|---|---|
| 2,946,725 A | 7/1960 | Norris et al. | |
| 3,070,510 A | 12/1962 | Cooley et al. | |
| 3,535,421 A | 10/1970 | Briner et al. | |
| 3,678,154 A | 7/1972 | Widder et al. | |
| 3,882,228 A | 5/1975 | Boncey et al. | |
| 3,937,807 A | 2/1976 | Haefele | |
| 3,959,458 A | 5/1976 | Agricola et al. | |
| 3,988,433 A | 10/1976 | Benedict | |
| 4,051,234 A | 9/1977 | Gieske et al. | |
| 4,083,955 A | 4/1978 | Grabenstetter et al. | |
| 4,136,163 A | 1/1979 | Watson et al. | |
| 4,138,477 A | 2/1979 | Gaffar | |
| 4,157,387 A | 6/1979 | Benedict | |
| 4,183,914 A | 1/1980 | Gaffar et al. | |
| 4,206,215 A | 6/1980 | Bailey | |
| 4,305,502 A | 12/1981 | Gregory et al. | |
| 4,371,516 A | 2/1983 | Gregory et al. | |
| 4,374,824 A | 2/1983 | Wahmi | |
| 4,443,430 A | 4/1984 | Mattei et al. | |
| 4,459,425 A | 7/1984 | Amano et al. | |
| 4,528,180 A | 7/1985 | Schaeffer | |
| 4,627,977 A | 12/1986 | Gaffar et al. | |
| 4,640,943 A | 2/1987 | Meguro et al. | |
| 4,642,903 A | 2/1987 | Davies | |
| 4,684,528 A * | 8/1987 | Godfrey | 426/74 |
| 4,687,662 A | 8/1987 | Schobel | |
| 4,849,213 A | 7/1989 | Schaeffer | |
| 4,894,220 A | 1/1990 | Nabi et al. | |
| 4,946,684 A | 8/1990 | Blank et al. | |
| 5,015,466 A | 5/1991 | Parran, Jr. et al. | |
| 5,145,666 A | 9/1992 | Lukacovic et al. | |
| 5,180,577 A | 1/1993 | Polefka et al. | |
| 5,188,825 A | 2/1993 | Iles et al. | |
| 5,198,220 A | 3/1993 | Damani | |
| 5,213,790 A | 5/1993 | Lukacovic et al. | |
| 5,215,756 A | 6/1993 | Gole et al. | |
| 5,242,910 A | 9/1993 | Damanj | |
| 5,281,410 A | 1/1994 | Lukacovic et al. | |
| 5,298,261 A | 3/1994 | Pebley et al. | |
| 5,989,524 A | 11/1999 | Dromard et al. | |
| 6,579,929 B1 * | 6/2003 | Cole et al. | 524/492 |
| 2003/0165442 A1 * | 9/2003 | Baig et al. | 424/57 |
| 2006/0018966 A1 * | 1/2006 | Lin et al. | 424/484 |
| 2006/0105052 A1 | 5/2006 | Acar et al. | |
| 2007/0104660 A1 | 5/2007 | Miksa et al. | |
| 2007/0116831 A1 * | 5/2007 | Prakash et al. | 426/548 |
| 2007/0122359 A1 | 5/2007 | Wang et al. | |
| 2008/0213883 A1 | 9/2008 | Davis et al. | |
| 2009/0319052 A1 | 12/2009 | Butler et al. | |

FOREIGN PATENT DOCUMENTS

| | | |
|---|---|---|
| CA | 1127089 | 7/1982 |
| CN | 1377252 | 10/2002 |
| GB | 1506045 | 4/1978 |
| JP | 05-310544 | * 11/1993 |
| JP | 2001-247310 | 9/2001 |
| JP | 2006-151877 | 6/2006 |
| WO | WO 95/11671 | 5/1995 |
| WO | WO 95/33446 | 12/1995 |
| WO | WO 01/10392 | 2/2001 |
| WO | WO 2005/063185 | 7/2005 |
| WO | WO 2006/100071 | 9/2006 |
| WO | WO 2007/059438 | 5/2007 |
| WO | WO 2008/015117 | 2/2008 |
| WO | WO 2008/068149 | 6/2008 |
| WO | WO 2009/103651 | 8/2009 |

OTHER PUBLICATIONS

International Search Report and Written Opinion in International Application No. PCT/US09/039198 mailed May 3, 2010.
Jal et al., 2004, "Chemical modification of silica surface by immobilization of functional groups for extractive concentration of metal ions," Talanta 62(5):1005-1028.
Koprivova et al., 1984, "Antibacterial Component of Cosmetics and Pharmaceuticals," CA Plus Database Accession No. 1986:613952.
Lussi et al., 1995, "Prediction of the erosive potential of some beverages," Caries Res. 29(5):349-354.
Kitadai et al., 2009, "ATR-IR Spectroscopic Study of L-Lysine Adsorption on Amorphous Silica," J. Colloid and Interface Science 329(1):31-37.

\* cited by examiner

*Primary Examiner* — Lezah Roberts
(74) *Attorney, Agent, or Firm* — Anne Louise St. Martin

(57) ABSTRACT

The invention encompasses compositions and methods for treating and modifying surfaces of teeth, which compositions include calcium and magnesium containing silicates or silica, cationic polymer modified silica or combinations thereof. The composition when applied to the teeth or a tooth surface deposit on such surfaces to repair acid damaged enamel and prevent further erosion of a tooth surface.

23 Claims, No Drawings

DENTIFRICE COMPOSITIONS AND METHODS FOR TREATING AND PREVENTING DAMAGE TO TOOTH SURFACES

CROSS-REFERENCE TO RELATED APPLICATION

The present application is a national stage entry under 35 U.S.C. §371 of International Patent Application No. PCT/US2009/039198, filed Apr. 1, 2009, the entirety of which is hereby incorporated by reference.

FIELD OF THE INVENTION

The invention encompasses compositions and methods for treating and modifying surfaces of teeth, which compositions include calcium and magnesium containing silicates or silica, cationic polymer modified silica or combinations thereof. The composition when applied to the teeth or a tooth surface deposit on such surfaces to repair acid damaged enamel and prevent further erosion of a tooth surface.

BACKGROUND OF THE INVENTION

Dental caries is initiated by localized demineralization of hard tissue of the teeth usually by organic acids produced from fermentation of dietary sugar by dental plaque or dentopathogenic bacteria. Even though the prevalence of dental caries has decreased using fluoride in most developed countries, the disease remains a major public health problem. Dental erosion is a chemically drive rapid, normally non-localized process resulting in the irreversible loss of tooth mineral by dietary or regurgitated acids. Gingivial recession abrasion and acid erosion are primary factors that can expose dentin tubules facilitating dentil hypersensitivity. Dental hypersensitivity is due to exposed dentinal tubules through loss of the protective mineralized layer, the cementum. Dental calculus is the unwanted accretion of calcium phosphate minerals on the tooth surface. All these conditions, dental caries, dental erosion, dental hypersensitivity and dental calculus are therefore imbalances in the level of calcium phosphates in the teeth.

Dental erosion may be caused by extrinsic or intrinsic factors. Extrinsic erosion is the result of oral consumption of dietary acids such as acidic beverages or fruit juices and environmental factors such as exposure to airborne contamination or acidic water.

The incidence and severity of dental erosion is on the rise with the increase in the consumption of acidic beverages and juices. The pH and titratable acidity of acidic beverages have been identified as the main causative agents in the initiation and progression of dental erosion. (See, e.g., Lussi, 1995, *Caries Res.* 29, 349).

SUMMARY OF THE INVENTION

The inventors have developed compositions and methods useful for treating or preventing dental erosion, particularly erosion of the enamel of a tooth or tooth surface.

The invention encompasses a chemical barrier technology that deposits minerals to damaged or softened enamel and forms a semi-impermeable matrix on the dentition. This unique surface matrix counteracts and protect the dentition from acid attack to reduce mineral loss and repair acid accelerated wear and structural depressions on the dentition surface In addition, the compositions of the invention provide barrier on the teeth or a tooth surface that acts as a proton sink to neutralize acid and prevent it from further dissolving native enamel.

In one embodiment, the invention encompasses dentifrice compositions including a cationically modified silica in an amount effective to treat or prevent erosive damage to an enamel surface of a tooth.

In another embodiment, the invention encompasses dentifrice compositions including calcium containing silicates and silica, magnesium-containing silicates and silica, and combinations thereof in an amount effective to treat or prevent erosive damage to an enamel surface of a tooth.

The invention also encompasses methods of treating or preventing erosive damage to an enamel surface of a tooth including administering to a subject in need thereof an effective amount of a composition comprising a cationically modified silica, calcium containing silicates and silica, magnesium containing silicates and silica, and combinations thereof.

These and other features, aspects, and advantages of the present invention will become evident to those skilled in the art from the following detailed description.

DETAILED DESCRIPTION OF THE INVENTION

Definitions

While the specification concludes with claims, which particularly point out and distinctly claim the invention, it is believed the present invention will be better understood from the following description.

All percentages and ratios used herein are by weight of the specific oral composition and not of the overall oral formulation that is delivered, unless otherwise specified. All measurements are made at 25° C., unless otherwise specified.

By "oral composition" is meant a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. The oral composition of the invention may be in the form of a toothpaste, dentifrice, tooth powder, tooth gel, subgingival gel, mouthrinse, denture product, mouthspray, lozenge, oral tablet, or chewing gum. The oral composition may also be incorporated onto strips or films for direct application or attachment to oral surfaces.

The term "dentifrice" as used herein, means paste, gel, or liquid formulations unless otherwise specified. The dentifrice composition may be a single-phase composition or may be a combination of two or more separate dentifrice compositions. The dentifrice composition may be in any desired form, such as deep striped, surface striped, multilayered, having the gel surrounding the paste, or any combination thereof.

The term "dispenser" as used herein, means any pump, tube, or container suitable for dispensing compositions such as dentifrices.

The term "teeth" as used herein, refers to natural teeth as well as artificial teeth or dental prosthesis.

The term "orally acceptable carrier" as used herein means any safe and effective materials for use in the compositions of the present invention. Such materials include fluoride ion sources, anticalculus agents, buffers, abrasive polishing materials, peroxide sources, alkali metal bicarbonate salts, thickening materials, humectants, water, surfactants, titanium dioxide, flavor system, sweetening agents, xylitol, coloring agents, and mixtures thereof.

Herein, the terms "tartar" and "calculus" are used interchangeably and refer to mineralized dental plaque deposits.

The term "treating", as used herein, refers to a detectable improvement in an adverse condition and/or a lessening the symptoms of the condition upon contacting a mammal with an oral composition of the invention and/or according to a method of the invention. By way of a non-limiting example, treating demineralization of a tooth surface may comprise halting or preventing any further demineralization after treatment has taken place. In an aspect, a treatment may be a partial treatment, wherein demineralization is slowed from the rate or extent to which it occurred prior to treatment. In another aspect, treatment may comprise a partial and/or complete reversal of demineralization, in which re-mineralization occurs to a degree.

The term "preventing" as used herein refers to the prevention of a particular condition, state or event. By way of a non-limiting example, prevention of demineralization may encompass completely preventing any demineralization of a tooth. In another aspect, preventing demineralization may encompass partial prevention, wherein demineralization takes place at a slower rate or to a lesser extent than which it would have in the absence of a preventative treatment and/or composition according to the invention, as applied to a tooth surface.

General Description of the Invention

The invention general encompasses dentifrice compositions that provide a chemical barrier to one or more tooth surfaces that deposits silica to softened enamel and forms a semi-impermeable coating on the dentition for the repair of damaged enamel and the prevention of further erosive damage, for example, by acids.

In one embodiment, the invention encompasses dentifrice compositions including a cationically modified silica in an amount effective to treat or prevent erosive damage to an enamel surface of a tooth.

In certain embodiments, the cationically modified silica comprises silica covalently bonded to positively charged amino acid.

In other embodiments, the positively charged amino acid is lysine.

In other embodiments, the cationically modified silica comprises silica covalently bonded to positively charged peptide.

In other embodiments, the positively charged peptide is polylysine.

In other embodiments, the cationically modified silica comprises silica covalently bonded a silane.

In other embodiments, the silane includes aminosilanes, glycidoxysilanes, mercaptosilanes, and combinations thereof.

In other embodiments, the aminosilane comprises (3-aminopropyl)-triethoxysilane, (3-aminopropyl)-diethoxy-methylsilane, (3-aminopropyl)-dimethyl-ethoxysilane, and combination thereof.

In other embodiments, the glycidoxysilane comprises (3-glycidoxypropyl)-dimethyl-ethoxysilane.

In other embodiments, the mercaptosilane comprises (3-mercaptopropyl)-trimethoxysilane, (3-mercaptopropyl)-methyl-dimethoxysilane, and combinations thereof.

In other embodiments, the amount of cationically modified silica effective to treat or prevent erosive damage to an enamel surface of a tooth is 0.01 wt. % to 30 wt. % based on the weight of the composition.

In other embodiments, the amount of cationically modified silica effective to treat or prevent erosive damage to an enamel surface of a tooth is 0.05 wt. % to 20 wt. % based on the weight of the composition.

In other embodiments, the amount of cationically modified silica effective to treat or prevent erosive damage to an enamel surface of a tooth is 0.1 wt. % to 10 wt. % based on the weight of the composition.

In other embodiments, the amount of cationically modified silica effective to treat or prevent erosive damage to an enamel surface of a tooth is 1 wt. % to 5 wt. % based on the weight of the composition.

In other embodiments, the compositions further include an abrasive, binder, surfactant, humectant, source of fluoride, and combinations thereof.

In other embodiments, the composition is a toothpaste.

In another embodiment, the invention encompasses dentifrice compositions including calcium containing silicates and silica, magnesium-containing silicates and silica, and combinations thereof in an amount effective to treat or prevent erosive damage to an enamel surface of a tooth.

In certain embodiments, the silicates include nesosilicates (or orthosilicates), sorosilicates, cyclosilicates, tectosilicates, inosilicates (single chain), inosilicates (double chain), and phyllosilicates, and combinations thereof.

In other embodiments, the silica is colloidal silica.

In other embodiments, the silica is silica gel.

In other embodiments, the amount of calcium containing silicates and silica, magnesium-containing silicates and silica, and combinations thereof effective to treat or prevent erosive damage to an enamel surface of a tooth is 0.01 wt. % to 30 wt. % based on the weight of the composition.

In other embodiments, the amount of calcium containing silicates and silica, magnesium-containing silicates and silica, and combinations thereof effective to treat or prevent erosive damage to an enamel surface of a tooth is 0.05 wt. % to 20 wt. % based on the weight of the composition.

In other embodiments, the amount of calcium containing silicates and silica, magnesium-containing silicates and silica, and combinations thereof effective to treat or prevent erosive damage to an enamel surface of a tooth is 0.1 wt. % to 10 wt. % based on the weight of the composition.

In other embodiments, the amount of calcium containing silicates and silica, magnesium-containing silicates and silica, and combinations thereof effective to treat or prevent erosive damage to an enamel surface of a tooth is 1 wt. % to 5 wt. % based on the weight of the composition.

In other embodiments, the composition further includes an abrasive, binder, surfactant, humectant, source of fluoride, and combinations thereof.

In other embodiments, the composition is a toothpaste.

The invention also encompasses methods of treating or preventing erosive damage to an enamel surface of a tooth including administering to a subject in need thereof an effective amount of a composition comprising a cationically modified silica, calcium containing silicates and silica, magnesium containing silicates and silica, and combinations thereof.

In certain embodiments, the subject is a mammal.
In other embodiments, the subject is a human.
In other embodiments, the subject is a companion animal.
In other embodiments, the effective amount is 0.01 wt. % to 30 wt. % based on the weight of the composition.
In other embodiments, the effective amount is 0.05 wt. % to 20 wt. % based on the weight of the composition.
In other embodiments, the effective amount is 0.1 wt. % to 10 wt. % based on the weight of the composition.

In other embodiments, the effective amount is 1 wt. % to 5 wt. % based on the weight of the composition.

In other embodiments, the composition further includes an abrasive, binder, surfactant, humectant, source of fluoride, and combinations thereof.

In other embodiments, the composition is a toothpaste.

Compositions of the Invention

This invention encompasses compositions that deposit or provide a chemical barrier on a tooth surface to treat or prevent damage to tooth enamel and also provide for remineralization of a tooth or a tooth surface. In certain embodiments, the compositions of the invention are useful to treat or prevent disorders of the oral cavity associated with, for example, softened enamel. In certain embodiments, the compositions form a semi-impermeable coating on the dentition for the repair of damaged enamel and the prevention of further erosive damage to a tooth surface, for example, by acids.

Cationic Polymer Modified Silica

In one embodiment, the invention encompasses dentifrice compositions including a cationically modified silica in an amount effective to treat or prevent erosive damage to an enamel surface of a tooth.

In other embodiments, the invention encompasses compositions including cationically modified silica to provide enhanced surface adhesion and retention properties to the enamel or dentin surface to protect the enamel against acid induced erosive damage.

As used herein, the term "cationically modified silica" refers to any silica or silica particles that exhibit an overall positive surface charge. There are a number of ways to modify silica surfaces to form the cationically modified silica of the invention.

One illustrative method is via chemical modification by leveraging the strong reactivity of the hydroxyl groups on the silica surface. For example, in certain embodiments, the —OH groups on the silica surface can react with the carboxyl group on polymers to form an ester bond. In various embodiments, polymers, such as polylysine, can be attached to silica via the ester bond linkage. Since the lysine side chain is positive charged under neutral pH, the resulting silica-polylysine complex will exhibit a positive surface charge. Additional examples include covalently grafting a silane reagent to the silica, for example, by a silinization procedure. The silane compounds used in this procedure can contain either a primary or a secondary amine group to yield a net positive charge for the modified silica surface. In certain embodiments, the cationically modified silica includes silica covalently bonded to aminosilanes, for example, (3-aminopropyl)-triethoxysilane, (3-aminopropyl)-diethoxy-methylsilane, and (3-aminopropyl)-dimethyl-ethoxysilane, and combinations thereof; glycidoxysilanes, for example (3-glycidoxypropyl)-dimethyl-ethoxysilane; and mercaptosilanes, for example (3-mercaptopropyl)-trimethoxysilane, (3-mercaptopropyl)-methyl-dimethoxysilane, and combinations thereof.

Another illustrative method to modify the silica of the invention is via physical modification by capitalizing on the large surface area of silica. Surface porosity and negative charge to absorb cationically charged polymer species, such as, for example, chitosan. The chitosan-covered silica will exhibit a net positive charge. Through charge-charge interactions, the complex has enhanced surface adhesion and retention properties to negatively charged enamel or dentin surfaces. In addition, upon hydration, the polymers with extended polymer chains can interpenetrate the pellicle layer to form strong physical entanglements with the salivary protein that constitutes the pellicle. Both strong electrostatic and van der Waals interactions between the polymer on the silica surface and the enamel pellicle can enhance the residence time of the polymer-silica composite on the enamel and provide a good physical barrier for further acid attack.

In various embodiments, the silica of the invention can be any silica capable of being cationically modified, including, for example, silicas such as wet processed silica, dry processed silica, sol-gel processed silica and the like can be used as a raw material in the invention.

In general, any polymers can be used as the cationic polymer including, but not limited to, polymers having a primary to tertiary amine or a quaternary ammonium salt can suitably used, and the polymers having a quaternary ammonium salt are more suitable.

In various embodiments, the amounts of silica and the cationic polymer contained in the cationic polymer-modified silica shall not specifically be restricted. In various embodiments, the amount of silica contained in the silica dispersion is 1 wt. % to 50 wt. %, or 5 wt. % to 25 wt. % or 10 wt. % to 15 wt. %, and the amount of the cationic polymer is, for example, 3 to 50 parts by weight per 100 parts by weight of the silica.

In various embodiments, the silica particles in the cationic polymer-modified silica of the invention have to have a zeta potential, which is a barometer for a surface charge, of +10 mV, +20 mV, +30 mV, +40 mV, +50 mV, +60 mV or more.

In the cationic polymer-modified silica of the invention, the silica particles contained in the above have to have an average particle diameter of less than 1000 µm, 800 µm, 600 µm, 400 µm, 200 µm, 100 µm, 50 µm, 20 µm, 10 µm, or 5 µm.

Calcium ($Ca^{2+}$) and Magnesium ($Mg^{2+}$) Containing Silicates or Silica

The invention encompasses a chemical barrier technology that deposits minerals to damaged or softened enamel and forms a semi-impermeable coating on the dentition for the repair of damaged enamel and the prevention of further erosive damage to enamel by, for example, acids. In addition, the barrier of the invention acts as a proton sink to neutralize acid and prevent it from further dissolving native enamel.

In certain embodiments, the deposition of $Ca^{2+}$ or $Mg^{2+}$ silicates or $Ca^{2+}$ or $Mg^{2+}$ containing colloidal silica on acid eroded/challenged enamel surface can slowly release $Ca^{2+}$ and $Mg^{2+}$ to mineral depleted tooth surfaces.

In other embodiments, the silicates or silica barrier can prevent further acid attack by providing a physical barrier to block acid diffusion as well as a chemical barrier by neutralizing acids via an acid-base reaction.

The silicates of the invention generally include a compound containing an anion in which one or more central silicon atoms are surrounded by electronegative ligands. In certain embodiments, the silicates include silicon with oxygen as the ligand. Examples include, but are not limited to, nesosilicates (or orthosilicates) with isolated $[SiO_4]^{4-}$, sorosilicates with isolated double silicate tetrahedra groups with $(Si_2O_7)^{6-}$, cyclosilicates (ring silicates) with linked silicate tetrahedra with $(Si_nO_{3n})^{2x-}$, tectosilicates with a three-dimensional framework of silicate tetrahedra with $SiO_2$, inosilicates (single chain) with $[Si_nO_{3n}]^{2n-}$, inosilicates (double chain) with $[Si_{4n}O_{11n}]^{6n-}$, and phyllosilicates (sheet silicates) with parallel sheets of silicate tetrahedra with $Si_2O_5$.

In general, the silicate anions of the invention with a negative net charge have the charge balanced by other cations such as $Ca^{2+}$ and $Mg^{2+}$ to make an electrically neutral compound.

In certain embodiments, the calcium and magnesium silicates of the invention are water insoluble salts with excellent crystallization properties.

In other embodiments, the compositions of the invention include soluble Ca, Mg, and silicate salts to form in situ precipitation of Ca and Mg silicates. Without being limited by theory, the insoluble salt will crystallize on the surface of the dentin and enamel to prevent further erosive damage by acids and slowly release $Ca^{2+}$ and $Mg^{2+}$ to remineralize the enamel surface. In addition, the silicate barrier can prevent further acid attack by providing a physical barrier to block acid diffusion as well as a chemical barrier by neutralizing acids via an acid-base reaction. Ca and Mg silicates are basic in nature.

In other embodiments, the compositions of the invention can act as a $H^+$ sink to neutralize acid. The following equation is an example of an acid reaction with Ca or Mg silicates:

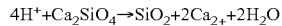
$$4H^+ + Ca_2SiO_4 \rightarrow SiO_2 + 2Ca_{2+} + 2H_2O$$

In certain embodiments, $Ca^{2+}$ or $Mg^{2+}$ will react with phosphate ligands on the acid challenged enamel surface to form Ca or Mg phosphate, remineralizing the surface of one or more teeth.

In other embodiments, deposition of $Ca^{2+}$ or $Mg^{2+}$ on an acid challenged tooth surface occurs by incorporating $Ca^{2+}$ or $Mg^{2+}$ salts in the colloidal network of silica. In various embodiments of the invention, there are a number of ways to entrap $Ca^{2+}$ and $Mg^{2+}$ salts, for example, in silica gel. In one illustrative embodiment, silica-calcium carbonate composite particles can be prepared by adding synthetic silica particles in the course of a carbonation reaction forming calcium carbonate and completing the carbonation reaction. The calcium carbonate, which is a first component of the two components constituting the composite particles of the invention, can include, for example, precipitated calcium carbonate. For example, one illustrative embodiment includes precipitated calcium carbonate as a surface portion and ground calcium carbonate as a core portion.

Precipitated calcium carbonate has various shapes and sizes of particles, and especially, when such precipitated calcium carbonate is used as calcium carbonate, the shape and size of precipitated calcium carbonate can be selected depending on the characteristics required for the intended silica-calcium carbonate composite particles, thus being suited for achieving the purposes of the invention.

In various embodiments, synthetic silica, which is a constituent of the composition of the invention, is artificially prepared through a chemical reaction and include colloidal silica, silica gel, anhydrous silica, white carbon and the like. These silicas, for example, have excellent characteristics such as a high specific surface area, high gas absorbability, fineness, high infiltration into fine interstices and adsorption, high adhesion, high oil absorption, uniformity of particles, high dispersability and the like.

Among these synthetic silicas, colloidal silica is made of amorphous silica having a round, chain-like, irregular or the like form and obtained by removing impurities from a silicic acid compound to provide a sol of silicic acid anhydride and controlling its pH and concentration to stabilize the sol. Silica gel consists of hydrous silicic acid obtained by decomposing sodium silicate with an inorganic acid. Anhydrous silica is one obtained by hydrolyzing silicon tetrachloride. White carbon is made of finely powdered hydrous silicic acid obtained by decomposing an organosilicon compound or sodium silicate.

Accordingly, in one embodiment, the invention encompasses oral care compositions including in an orally acceptable carrier at least 0.01%, at least 0.1 wt. %, at least 1 wt. %, at least 3 wt. %, at least 5 wt. %, at least 7 wt. %, at least 9 wt. %, 10 wt. %, 15 wt. %, 20 wt. %, 25 wt. %, 30 wt. %, 40 wt. %, 50 wt. % of a cationically modified silica, calcium containing silica and silicates, magnesium containing silica and silicates, and combinations thereof.

The oral compositions are useful to treat or prevent damage to enamel, enhance overall cleaning, inhibit plaque, whiten teeth, and enhance stain removal and prevention of staining of natural teeth and dental prosthesis.

In various embodiments, the compositions of the invention coat the teeth and act as a barrier to prevent or treat damage to the enamel of the teeth or a tooth surface.

Further, the compositions have the ability to act as a carrier for oral care actives such as bleaches and other teeth whitening agents, antimicrobials, fluoride, desensitizing agents, and flavors and to facilitate deposition and retention of these actives onto the oral surfaces where they can perform their intended function. It is believed the coating also acts as a protective barrier that retains the oral care active in close contact with the oral surface thereby ensuring that the activity such as bleaching or antimicrobial effect lasts longer. Effective bleaching will remove stains and lead to whiter teeth. Enhanced retention of antimicrobials on the oral surfaces will result in reducing the oral microorganisms that are causative agents of, or associated with, various dental diseases, including gingivitis, periodontal disease, and dental plaque.

The oral composition of the invention may be in the form of a dentifrice, toothpaste, tooth powder, topical oral gel, mouthrinse, denture product, mouthspray, lozenge, oral tablet, or chewing gum. The oral composition may also be incorporated onto strips or films for direct application or attachment to oral surfaces.

The oral care compositions in aqueous form will optimally have a pH ranging from 4 to 10. In certain embodiments, the pH of the compositions ranges from 5 to 8.

In addition to the components described above, the present oral care compositions may comprise additional components, which are described in the following paragraphs.

Orally Acceptable Carrier

In certain embodiments, the compositions of the invention also include an orally acceptable carrier to assist in the delivery of the compositions to a tooth surface.

The orally acceptable carrier includes one or more compatible solid or liquid filler diluents or encapsulating substances, which are suitable for topical oral administration. By "compatible," as used herein, is meant that the components of the composition are capable of being combined without interaction in a manner, which would substantially reduce the composition's stability and/or efficacy.

The carriers or excipients of the invention can include the usual and conventional components of dentifrices (including non-abrasive gels and gels for subgingival application), mouth rinses, mouth sprays, chewing gums, and lozenges (including breath mints) as more fully described hereinafter.

The choice of a carrier to be used is basically determined by the way the composition is to be introduced into the oral cavity. If a toothpaste (including tooth gels, etc.) is to be used, then a "toothpaste carrier" is chosen (comprising e.g., abrasive materials, sudsing agents, binders, humectants, flavoring and sweetening agents, etc.) as disclosed in e.g., U.S. Pat. No. 3,988,433, to Benedict. If a mouth rinse is to be used, then a "mouth rinse carrier" is chosen (comprising e.g., water, flavoring and sweetening agents, etc.), as disclosed in e.g., U.S. Pat. No. 3,988,433 to Benedict. Similarly, if a mouth spray is to be used, then a "mouth spray carrier" is chosen or if a lozenge is to be used, then a "lozenge carrier" is chosen (e.g., a candy base), candy bases being disclosed in, e.g., U.S. Pat. No. 4,083,955, to Grabenstetter et al.; if a chewing gum is to be used, a "chewing gum carrier" is chosen (comprising e.g., gum base, flavoring and sweetening agents), as disclosed in e.g., U.S. Pat. No. 4,083,955, to Grabenstetter et al. If a sachet is to be used, then a "sachet carrier" is chosen (e.g., sachet bag, flavoring and sweetening agents). If a subgingival gel is to be used (for delivery of actives into the periodontal pockets or around the periodontal pockets), then a "subgingival gel carrier" is chosen as disclosed in, e.g., U.S. Pat. No. 5,198,220, issued Mar. 30, 1993 and U.S. Pat. No. 5,242,910, issued Sep. 7, 1993, both to Damani. Other useful carriers include biphasic dentifrice formulations such as those disclosed in U.S. Pat. No. 5,213,790, issued May 23, 1993, U.S. Pat. No. 5,145,666, issued Sep. 8, 1992, and U.S. Pat. No. 5,281,410 issued Jan. 25, 1994 all to Lukacovic et al. and in U.S. Pat. Nos. 4,849,213 and 4,528,180 to Schaeffer. Carriers suitable for the preparation of compositions of the present invention are well known in the art. Their selection will depend on secondary considerations like taste, cost, and shelf stability, etc.

The compositions of the invention may be in the form of non-abrasive gels, including subgingival gels, which may be aqueous or non-aqueous. Aqueous gels generally include a thickening agent (from 0.1% to 20%), a humectant (from 10% to 55%), a flavoring agent (from 0.04% to 2%), a sweetening agent (from 0.1% to 3%), a coloring agent (from 0.01% to 0.5%), and the balance water. The compositions may comprise an anticaries agent (from 0.05% to 0.3% as fluoride ion), and an anticalculus agent (from 0.1% to 13%).

Compositions of the invention may also be in the form of dentifrices, such as toothpastes, tooth gels and tooth powders. Components of such toothpaste and tooth gels generally include one or more of a dental abrasive (from 5% to 50%), a surfactant (from 0.5% to 10%), a thickening agent (from 0.1% to 5%), a humectant (from 10% to 55%), a flavoring agent (from 0.04% to 2%), a sweetening agent (from 0.1% to 3%), a coloring agent (from 0.01% to 0.5%) and water (from 2% to 45%). Such toothpaste or tooth gel may also include one or more of an anticaries agent (from 0.05% to 0.3% as fluoride ion), and an anticalculus agent (from 0.1% to 13%). Tooth powders, of course, contain substantially all non-liquid components.

Other compositions of the subject invention are mouthwashes, including mouth sprays. Components of such mouthwashes and mouth sprays typically include one or more of water (from 45% to 95%), ethanol (from 0% to 25%), a humectant (from 0% to 50%), a surfactant (from 0.01% to 7%), a flavoring agent (from 0.04% to 2%), a sweetening agent (from 0.1% to 3%), and a coloring agent (from 0.001% to 0.5%). Such mouthwashes and mouth sprays may also include one or more of an anticaries agent (from 0.05% to 0.3% as fluoride ion), and an anticalculus agent (from 0.1% to 3%).

Other compositions of the invention are dental solutions including irrigation fluids. Components of such dental solutions generally include one or more of water (from 90% to 99%), preservative (from 0.01% to 0.5%), thickening agent (from 0% to 5%), flavoring agent (from 0.04% to 2%), sweetening agent (from 0.1% to 3%), and surfactant (from 0% to 5%).

Chewing gum compositions typically include one or more of a gum base (from 50% to 99%), a flavoring agent (from 0.4% to 2%) and a sweetening agent (from 0.01% to 20%).

The term "lozenge" as used herein includes: breath mints, troches, pastilles, microcapsules, and fast-dissolving solid forms including freeze dried forms (cakes, wafers, thin films, tablets) and compressed tablets. The term "fast-dissolving solid form" as used herein means that the solid dosage form dissolves in less than 60 seconds, less than 15 seconds, less than 5 seconds, after placing the solid dosage form in the oral cavity. Fast-dissolving solid forms are disclosed in commonly assigned WO 95/33446 and WO 95/11671; U.S. Pat. Nos. 4,642,903; 4,946,684; 4,305,502; 4,371,516; 5,188,825; 5,215,756; 5,298,261; 3,882,228; 4,687,662; 4,642,903.

In still another aspect, the invention provides a dental implement impregnated with the present composition. The dental implement comprises an implement for contact with teeth and other tissues in the oral cavity, said implement being impregnated with a composition of the invention. The dental implement can be impregnated fibers including dental floss or tape, chips, strips, films and polymer fibers.

Miscellaneous Carriers

Water employed in the preparation of commercially suitable oral compositions can be of low ion content and free of organic impurities. Water generally comprises 5% to 80%, and 20% to 50%, by weight of an aqueous composition herein. These amounts of water include the free water, which is added plus that which is introduced with other materials, such as with sorbitol.

Poloxamers may also be employed in the compositions. A poloxamer is classified as a nonionic surfactant. It may also function as an emulsifying agent, binder, stabilizer, and other related functions. Poloxamers are difunctional block-polymers terminating in primary hydroxyl groups with molecular weights ranging from 1,000 to above 15,000. Poloxamers are sold under the tradename of Pluronics and Pluraflo by BASF. Poloxamers for this invention include Poloxamer 407 and Pluraflo L4370.

Other emulsifying agents that may be used in the present compositions include polymeric emulsifiers such as the Pemulen series available from B.F. Goodrich, and which are predominantly high molecular weight polyacrylic acid polymers useful as emulsifiers for hydrophobic substances.

Titanium dioxide may also be added to the present composition. Titanium dioxide is a white powder which adds opacity to the compositions. Titanium dioxide generally comprises from 0.25% to 5% by weight of the dentifrice compositions.

The pH of the present compositions is adjusted through the use of buffering-agents. Non-chelating buffering agents and systems, as used herein, refer to agents that can be used to adjust the pH of the compositions to a range of pH 4 to pH 10. Buffering agents include monosodium phosphate, trisodium phosphate, sodium hydroxide, sodium carbonate, disodium hydrogen phosphate, sodium dihydrogen phosphate, potassium tartarate, and linear and cyclic polyphosphates. Buffering agents can be administered at a level of from 0.5% to 10%, by weight of the present compositions. The pH of dentifrice compositions is measured from a 3:1 aqueous slurry of dentifrice, for example, 3 parts water to 1 part dentifrice.

Other optional agents that may be used in the present compositions include dimethicone copolyols selected from alkyl- and alkoxy-dimethicone copolyols, such as C12 to C20 alkyl dimethicone copolyols and mixtures thereof including cetyl dimethicone copolyol marketed under the Trade Name Abil EM90. The dimethicone copolyol is generally present in a level of 0.01% to 25%, 0.1% to 5%, or 0.5% to 1.5% by weight. The dimethicone copolyols aid in providing positive tooth feel benefits.

Abrasives

The compositions of the invention can optionally include a dental abrasive. Dental abrasives useful in the compositions of the invention include many different materials. The material selected includes one, which is compatible within the composition of interest and does not excessively abrade dentin. Suitable abrasives include, for example, silicas including gels and precipitates, insoluble sodium polymetaphosphate, hydrated alumina, calcium carbonate, dicalcium orthophosphate dihydrate, calcium pyrophosphate, tricalcium phosphate, calcium polymetaphosphate, and resinous abrasive materials such as particulate condensation products of urea and formaldehyde.

Another class of abrasives for use in the present compositions is the particulate thermo-setting polymerized resin as described in U.S. Pat. No. 3,070,510. Suitable resins include, for example, melamines, phenolics, ureas, melamine-ureas, melamine-formaldehydes, urea-formaldehyde, melamine-urea-formaldehydes, cross-linked epoxides, and cross-linked polyesters.

Silica dental abrasives of various types can be used because of their unique benefits of exceptional dental cleaning and polishing performance without unduly abrading tooth enamel or dentine. The silica abrasive polishing materials herein, as well as other abrasives, generally have an average particle size ranging between 0.1 to 30 microns, or 1 to 15 microns. The abrasive can be precipitated silica or silica gels such as the silica xerogels.

Mixtures of abrasives can be used. The total amount of abrasive in dentifrice compositions of the subject invention is 6% to 70% by weight; toothpastes can contain from 10% to 50% of abrasives, by weight of the composition. Solution, mouth spray, mouthwash and non-abrasive gel compositions of the subject invention typically contain no abrasive.

Surfactants

In certain embodiments, the compositions of the invention also include a surfactant, including sarcosinate surfactants, isethionate surfactants and taurate surfactants. In certain embodiments, for use herein are alkali metal or ammonium salts of these surfactants. In other embodiments, the sodium and potassium salts of the following: lauroyl sarcosinate, myristoyl sarcosinate, palmitoyl sarcosinate, stearoyl sarcosinate and oleoyl sarcosinate.

The surfactant can be present in the compositions of the invention is present in an amount of 0.1% to 2.5%, 0.3% to 2.5% or 0.5% to 2% by weight of the total composition.

Other suitable compatible surfactants can optionally be used or in combination with the sarcosinate surfactant in the compositions of the invention. Suitable optional surfactants are described more fully in U.S. Pat. No. 3,959,458, May 25, 1976 to Agricola et al.; U.S. Pat. No. 3,937,807, Feb. 10, 1976 to Haefele; and U.S. Pat. No. 4,051,234, Sep. 27, 1988 to Gieske et al.

Anionic surfactants useful herein include the water-soluble salts of alkyl sulfates having from 10 to 18 carbon atoms in the alkyl radical and the water-soluble salts of sulfonated monoglycerides of fatty acids having from 10 to 18 carbon atoms. Sodium lauryl sulfate and sodium coconut monoglyceride sulfonates are examples of anionic surfactants of this type. Mixtures of anionic surfactants can also be utilized.

Cationic surfactants useful in the present invention can be broadly defined as derivatives of aliphatic quaternary ammonium compounds having one long alkyl chain containing from 8 to 18 carbon atoms such as lauryl trimethylammonium chloride; cetyl pyridinium chloride; cetyl trimethylammonium bromide; di-isobutylphenoxyethyl-dimethylbenzylammonium chloride; coconut alkyltrimethylammonium nitrite; cetyl pyridinium fluoride; etc. Other compounds are the quaternary ammonium fluorides described in U.S. Pat. No. 3,535,421, Oct. 20, 1970, to Briner et al., where said quaternary ammonium fluorides have detergent properties. Certain cationic surfactants can also act as germicides in the compositions disclosed herein. Cationic surfactants include chlorhexidine. Persons skilled in the art are aware of this possibility and should incorporate cationic surfactants only with this limitation in mind.

Nonionic surfactants that can be used in the compositions of the invention can be broadly defined as compounds produced by the condensation of alkylene oxide groups (hydrophilic in nature) with an organic hydrophobic compound which may be aliphatic or alkylaromatic in nature. Examples of suitable nonionic surfactants include the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

Zwitterionic synthetic surfactants useful in the invention can be broadly described as derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water-solubilizing group, e.g., carboxy, sulfonate, sulfate, phosphate or phosphonate.

Betaine surfactants are disclosed in U.S. Pat. No. 5,180,577 to Polefka et al., issued Jan. 19, 1993. Typical alkyl dimethyl betaines include decyl betaine or 2-(N-decyl-N,N-dimethylammonio)acetate, coco betaine or 2-(N-coco-N,N-dimethyl ammonio)acetate, myristyl betaine, palmityl betaine, lauryl betaine, cetyl betaine, cetyl betaine, stearyl betaine, etc. The amidobetaines are exemplified by cocoamidoethyl betaine, cocoamidopropyl betaine, lauramidopropyl betaine and the like. The betaines of choice are the cocoamidopropyl betaine and the lauramidopropyl betaine.

Anticalculus Agent

In certain embodiments, the compositions of the invention also include an anticalculus agent, for example, synthetic anionic polymers, including polyacrylates and copolymers of maleic anhydride or acid and methyl vinyl ether (e.g., Gantrez), as described, for example, in U.S. Pat. No. 4,627,977; as well as, for example, polyamino propane sulfonic acid (AMPS), zinc citrate trihydrate, polypeptides (such as polyaspartic and polyglutamic acids), and mixtures thereof.

Chelating Agents

In certain embodiments, the compositions of the invention also include a chelating agent such as tartaric acid. Chelating agents are able to complex calcium found in the cell walls of the bacteria. Chelating agents can also disrupt plaque by removing calcium from the calcium bridges which help hold this biomass intact. It is important to not however, it is not desired to use a chelating agent which has an affinity for calcium that is too high, as this may result in tooth demineralization from the chemically reactive and friable acid eroded dentition surface, which is contrary to the objects and intentions of the present invention.

Chelating agents include alkali metal salts of tartaric acid, disodium tartrate, dipotassium tartrate, sodium potassium tartrate, sodium hydrogen tartrate and potassium hydrogen tartrate. The amounts of chelating agent suitable for use in the invention are 0.1% to 2.5%, 0.5% to 2.5% and 1% to 2.5%. The tartaric acid salt chelating agent can be used alone or in combination with other optional chelating agents. The chelating agents have a calcium binding constant of $10^1$ to $10^5$ to provide improved cleaning with reduced plaque and calculus formation.

Still another possible group of chelating agents suitable for use in the present invention are the anionic polymeric polycarboxylates. Such materials are well known in the art, being employed in the form of their free acids or partially or fully neutralized water soluble alkali metal (e.g. potassium and sodium) or ammonium salts. 1:4 to 4:1 copolymers of maleic anhydride or acid with another polymerizable ethylenically unsaturated monomer, for example, methyl vinyl ether (methoxyethylene) having an average molecular weight (AMW) of 30,000 to 1,000,000. These copolymers are available for example as Gantrez AN 139 (AMW 500,000), AN 119 (AMW 250,000) and S-97 Pharmaceutical Grade (AMW 70,000), of GAF Chemicals Corporation.

Other polymeric polycarboxylates include those such as the 1:1 copolymers of maleic anhydride with ethyl acrylate, hydroxyethyl methacrylate, N-vinyl-2-pyrrolidone, or ethylene, the latter being available for example as Monsanto EMA No. 1103, AMW 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Additional polymeric polycarboxylates are disclosed in U.S. Pat. No. 4,138,477, Feb. 6, 1979 to Gaffar and U.S. Pat. No. 4,183,914, Jan. 15, 1980 to Gaffar et al. and include copolymers of maleic anhydride with styrene, isobutylene or ethyl vinyl ether, polyacrylic, polyitaconic and polymaleic acids, and sulfoacrylic oligomers of AMW as low as 1,000 available as Uniroyal ND-2.

Fluoride Source

In certain embodiments, the compositions of the invention also include a water-soluble fluoride compound present in dentifrices and other oral compositions in an amount sufficient to give a fluoride ion concentration in the composition at 25° C., and/or when it is used of from 0.0025% to 5% by weight, from 0.005% to 2% by weight, to provide additional anticaries effectiveness. A wide variety of fluoride ion-yielding materials can be employed as sources of soluble fluoride in the present compositions. Examples of suitable fluoride ion-yielding materials are found in U.S. Pat. No. 3,535,421, Oct. 20, 1970 to Briner et al. and U.S. Pat. No. 3,678,154, Jul. 18, 1972 to Widder et al. Representative fluoride ion sources include stannous fluoride, sodium fluoride, potassium fluoride, sodium monofluorophosphate, amine fluoride and others including mixtures thereof.

Teeth Whitening Actives and Teeth Color Modifying Substances

In certain embodiments, the compositions of the invention also include bleaching agents, teeth whitening agents, teeth color modifying substances may also be included among the oral care actives useful in the invention. These substances are suitable for modifying the color of the teeth to satisfy the consumer. These substances comprise particles that when applied on the tooth surface modify that surface in terms of absorption and, or reflection of light. Such particles provide an appearance benefit when a film containing such particles is applied over the surfaces of a tooth or teeth.

The levels of colorants are generally used in the range of 0.05% to 20%, 0.10% to 15% or 0.25% to 10% of the composition.

Thickening Agents

In certain embodiments, the compositions of the invention also include thickening materials to provide a desirable consistency of the composition, to provide desirable active release characteristics upon use, to provide shelf stability, and to provide stability of the composition, etc. Thickening agents include carboxyvinyl polymers, carrageenan, hydroxyethyl cellulose, laponite and water soluble salts of cellulose ethers such as sodium carboxymethylcellulose and sodium carboxymethyl hydroxyethyl cellulose. Nonionic charged polymers such as hydrophobically modified starch, polyethyleneoxide, natural gums such as aloe, vora hyaluronic acid glucan, gum karaya, xanthan gum, gum arabic, and gum tragacanth can also be used. Colloidal magnesium aluminum silicate or finely divided silica can be used as part of the thickening agent to further improve texture.

Thickening or gelling agents include a class of homopolymers of acrylic acid crosslinked with an alkyl ether of pentaerythritol or an alkyl ether of sucrose, or carbomers.

Copolymers of lactide and glycolide monomers, the copolymer having the molecular weight in the range of from 1,000 to 120,000 (number average), are useful for delivery of actives into the periodontal pockets or around the periodontal pockets as a "subgingival gel carrier." These polymers are described in U.S. Pat. No. 5,198,220, issued Mar. 30, 1993 and U.S. Pat. No. 5,242,910, issued Sep. 7, 1993, both to Damani, and U.S. Pat. No. 4,443,430, to Mattei, issued Apr. 17, 1984.

Thickening agents in an amount of 0.1% to 15%, 2% to 10%, or 4% to 8%, by weight of the total toothpaste or gel composition, can be used. Higher concentrations can be used for chewing gums, lozenges (including breath mints), sachets, non-abrasive gels and subgingival gels.

Humectants

In certain embodiments, the compositions of the invention also include a humectant. The humectant serves to keep toothpaste compositions from hardening upon exposure to air, to give compositions a moist feel to the mouth, and, for particular humectants, to impart desirable sweetness of flavor to toothpaste compositions. The humectant, on a pure humectant basis, generally comprises 0% to 70%, 5% to 25%, by weight of the compositions herein. Suitable humectants for use in compositions of the subject invention include edible polyhydric alcohols such as glycerin, sorbitol, xylitol, butylene glycol, polyethylene glycol, and propylene glycol, especially sorbitol and glycerin.

Flavoring and Sweetening Agents

In certain embodiments, the compositions of the invention also include flavoring agents. Suitable flavoring agents include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, and mixtures thereof. Flavoring agents are generally used in the compositions at levels of 0.001% to 5%, by weight of the composition.

Sweetening agents which can be used include sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame and cyclamate salts, especially sodium cyclamate and sodium saccharin, and mixtures thereof. A composition contains 0.1% to 10% of these agents, or 0.1% to 1%, by weight of the composition.

In addition to flavoring and sweetening agents, coolants, salivating agents, warming agents, and numbing agents can be used as optional ingredients in compositions of the present invention. These agents are present in the compositions at a level of 0.001% to 10%, or 0.1% to 1%, by weight of the composition.

The coolant can be any of a wide variety of materials. Included among such materials are carboxamides, menthol, ketals, diols, and mixtures thereof. Coolants in the compositions include the paramenthan carboxyamide agents such as N-ethyl-p-menthan-3-carboxamide, known commercially as "WS-3", N,2,3-trimethyl-2-isopropylbutanamide, known as "WS-23," and mixtures thereof. Additional coolants are selected from the group consisting of menthol, 3-1-menthoxypropane-1,2-diol known as TK-10 manufactured by Takasago, menthone glycerol acetal known as MGA manufactured by Haarmann and Reimer, and menthyl lactate known as Frescolat manufactured by Haarmann and Reimer. The terms menthol and menthyl as used herein include dextro- and levorotatory isomers of these compounds and racemic mixtures thereof. TK-10 is described in U.S. Pat. No. 4,459,425, Amano et al., issued Jul. 10, 1984. WS-3 and other agents are described in U.S. Pat. No. 4,136,163, Watson, et al., issued Jan. 23, 1979.

Salivating agents of the invention include Jambu manufactured by Takasago. Warming agents include capsicum and nicotinate esters, such as benzyl nicotinate. Numbing agents include benzocaine, lidocaine, clove bud oil, and ethanol.

Alkali Metal Bicarbonate Salt

In certain embodiments, the compositions of the invention also include an alkali metal bicarbonate salt. Alkali metal bicarbonate salts are soluble in water and unless stabilized, tend to release carbon dioxide in an aqueous system. Sodium bicarbonate, also known as baking soda, is an alkali metal bicarbonate salt. The composition may contain 0.5% to 30%, 0.5% to 15%, or 0.5% to 5% of an alkali metal bicarbonate salt.

Other Active Agents

In certain embodiments, the compositions of the invention also include other active agents, such as antimicrobial agents. Included among such agents are water insoluble non-cationic antimicrobial agents such as halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, and halogenated carbanilides. The water soluble antimicrobials include quaternary ammonium salts and bis-biquamide salts, among others. Triclosan monophosphate is an additional water soluble antimicrobial agent. The quaternary ammonium agents include those in which one or two of the substitutes on the quaternary nitrogen has a carbon chain length (typically alkyl group) from 8 to 20, typically from 10 to 18 carbon atoms while the remaining substitutes (typically alkyl or benzyl group) have a lower number of carbon atoms, such as from 1 to 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl)ammonium bromide, benzyl dimethylstearyl ammonium chloride, cetyl pyridinium chloride, quaternized 5-amino-1,3-bis(2-ethyl-hexyl)-5-methylhexahydropyrimidine, benzalkonium chloride, benzethonium chloride and methyl benzethonium chloride are exemplary of typical quaternary ammonium antibacterial agents. Other compounds are bis[4-(R-amino)-1-pyridinium]alkanes as disclosed in U.S. Pat. No. 4,206,215, issued Jun. 3, 1980, to Bailey. Other antimicrobials such as copper bisglycinate, copper glycinate, zinc citrate, and zinc lactate may also be included. Enzymes are another type of active that may be used in the present compositions. Useful enzymes include those that belong to the category of proteases, lytic enzymes, plaque matrix inhibitors and oxidases: Proteases include papain, pepsin, trypsin, ficin, bromelin; cell wall lytic enzymes include lysozyme; plaque matrix inhibitors include dextranases, mutanases; and oxidases include glucose oxidase, lactate oxidase, galactose oxidase, uric acid oxidase, peroxidases including horse radish peroxidase, myeloperoxidase, lactoperoxidase, chloroperoxidase. The oxidases also have whitening/cleaning activity, in addition to antimicrobial properties. Such agents are disclosed in U.S. Pat. No. 2,946,725, Jul. 26, 1960, to Norris et al. and in U.S. Pat. No. 4,051,234, Sep. 27, 1977 to Gieske et al. Other antimicrobial agents include chlorhexidine, triclosan, triclosan monophosphate, and flavor oils such as thymol. Triclosan and other agents of this type are disclosed in Parran, Jr. et al., U.S. Pat. No. 5,015,466, issued May 14, 1991, and U.S. Pat. No. 4,894,220, Jan. 16, 1990 to Nabi et al. These agents, which provide anti-plaque benefits, may be present at levels of from 0.01% to 5%, by weight of the dentifrice composition.

Methods of Treating and Preventing Disorders of the Oral Cavity

The invention also relates to methods for treating or preventing damage to the enamel of a tooth surface, cleaning and polishing teeth and reducing the incidence of stain, plaque, gingivitis and calculus on dental enamel.

The method of use herein comprises contacting a subject's dental enamel surfaces and oral mucosa with the oral compositions according to the invention. The method of use may be by brushing with a dentifrice, rinsing with a dentifrice slurry or mouthrinse, or chewing a gum product. Other methods include contacting the topical oral gel, mouthspray, or other form such as strips or films with the subject's teeth and oral mucosa. The composition may be applied directly to the teeth, gums, or other oral surface with a brush, a pen applicator, or the like, or even with the fingers. The subject may be any person or other animal whose tooth surface contacts the oral composition. By "other animal" is meant to include household pets or other domestic animals, or animals kept in captivity. For example, a method of use may include brushing a dog's teeth with one of the dentifrice compositions. Another example would include the rinsing of a cat's mouth with an oral composition for a sufficient amount of time to see a benefit. Pet care products such as chews and toys may be formulated to contain the present oral compositions.

The dentifrice compositions of the invention include, in part, cationic polymer modified silica, calcium containing silica and silicates, magnesium containing silica and silicates, and combinations thereof that is useful in treating or preventing various disorders of the oral cavity, for example, enamel remineralization, incipient caries remineralization, carious dentin remineralization, caries prevention, arresting decay, reversing decay, anti-caries, pit and fissure sealants, prophylactic pastes, fluoride treatments, dentinal sealants, and combinations thereof.

In one embodiment, a method of cleaning hypersensitive teeth includes contacting the teeth or a tooth surface of a subject in need thereof with a dentifrice composition of the invention.

In another embodiment, the invention encompasses a method of treating dental hypersensitivity including contacting the teeth or a tooth surface of a subject in need thereof with a dentifrice composition of the invention.

Additional methods of treating or preventing disorders of the oral cavity are also included within the scope of the invention. In one embodiment, a method of at least partially occluding dentin tubules of a subject in need thereof includes contacting the teeth or a tooth surface with a dentifrice composition of the invention. In one embodiment, a method of preventing tooth decay of a subject in need thereof includes contacting the teeth or a tooth surface with a dentifrice composition of the invention. In one embodiment, a method of treating tooth decay of a subject in need thereof includes contacting the teeth or a tooth surface with a dentifrice composition of the invention. In one embodiment, a method of preventing incipient carries of a subject in need thereof includes contacting the teeth or a tooth surface with a dentifrice composition of the invention. In one embodiment, a method of remineralizing enamel of a subject in need thereof includes contacting the teeth or a tooth surface with a dentifrice composition of the invention. In one embodiment, a method of sealing fissures of a subject in need thereof includes contacting the teeth or a tooth surface with a dentifrice composition of the invention. In one embodiment, a method of sealing pits of a subject in need thereof includes contacting the teeth or a tooth surface with a dentifrice composition of the invention. In one embodiment, a method of lining tooth structure of a subject in need thereof includes contacting the teeth or a tooth surface with a dentifrice composition of the invention. In one embodiment, a method for capping pulp of a subject in need thereof includes contacting the teeth or a tooth surface with a dentifrice composition of the invention. In one embodiment, a method for treating tooth structure after periodontal surgery of a subject in need thereof includes contacting the teeth or a tooth surface with a dentifrice composition of the invention.

EXAMPLES

The following examples further describe and demonstrate various embodiments within the scope of the present invention. These examples are given solely for the purpose of illustration and are not to be construed as limitations of the present invention as many variations thereof are possible without departing from the scope and spirit of the present invention.

Example 1

Method of Processing a Dentifrice Composition of the Invention

The following procedure is an exemplary dentifrice composition containing bioacceptable and bioactive glass.

1. A formula amount of glycerin is loaded to a suitable beaker. Saccharin, titanium dioxide, and gum are slowly added and mixed until well-dispersed. The beaker and contents are heated to 150° F. and are mixed for fifteen (15) minutes.

2. Pluracare® L1220 PEG/PPG co-polymer is added to the ross mixer pot. The contents of the beaker in Step 1 are transferred to the ross pot and are mixed for five (5) minutes with vacuum. After that time, the ross cover is opened and the temperature is checked. If the temperature is over 120° F., Step 2 is repeated. When the temperature cools to 120° F. or below, the sodium monofluorophosphate (MFP), calcium and magnesium containing silica or silicates (or cationic modified polymer silica) and silica abrasive (Zeodent® 114) are added and are mixed until the powders are wet. The vacuum is pulled, and the contents in the ross pot are mixed for twenty (20) minutes on high speed.

3. The temperature is checked. The temperature should be 110° F. or below. Flavor and sodium lauryl sulfate powder are added, then the composition is mixed for ten (10) minutes on high speed under full vacuum.

TABLE 1

Exemplary Compositions Containing Bioactive Glass

| Ingredient | Composition A | Composition B | Composition C | Composition D | Composition E |
|---|---|---|---|---|---|
| Glycerin | 63.2 | 46 | 63.4 | 63.5 | 52.5 |
| Pluracare ® L1220 | 5 | 22 | 5 | 5 | 5 |
| Sodium MFP | 1.1 | 1.1 | 1.1 | 1.1 | 1.1 |
| Saccharin | 0.3 | 0.3 | 0.3 | 0.3 | 0.3 |
| Titanium Dioxide | 1 | 1 | 1 | 1 | 1 |
| Mg and Ca contianing silicates or silica | 10 | 8 | 4 | 5 | 6 |
| Cationic polymer modified silica or silicates |  | 2 | 6 | 5 | 4 |
| Silica thickener (Zeodent ® 165) | 8 | 8 | 8 | 8 | 20 |
| Silica abrasive (Zeodent ® 114) | 8 | 8 | 8 | 8 | 2 |
| Flavor | 1.2 | 0.9 | 0.9 | 0.9 | 0.9 |
| SLS | 1.7 | 1.7 | 1.7 | 1.7 | 1.7 |

Example 2

A Dentifrice Composition Comprising a Cationically Modified Silica in an Amount Effective to Treat or Prevent Erosive Damage to an Enamel Surface of a Tooth

A composition of the invention may comprise cationically modified silica, wherein the amount of silica in the composition is effective to treat or prevent erosive damage to the enamel surface of a tooth. In an aspect, such an amount of silica can be determined by using any method known in the art. By way of a non-limiting example, a series of experimental studies can be conducted in which the silica concentration ranges from zero silica to a predetermined maximum concentration, wherein all aspects of each experimental example are identical except for the silica concentration. The degree to which demineralization is prevented can be ascertained for each sample. The concentrations of silica at which demineralization is prevented are indicative of concentrations of cationically modified silica in an amount effective to prevent demineralization to the tooth surface.

The invention is not to be limited in scope by the specific embodiments disclosed in the examples, which are intended as illustrations of a few aspects of the invention, and any embodiments, which are functionally equivalent, are within the scope of this invention. Indeed, various modifications of the invention in addition to those shown and described herein will become apparent to those skilled in the art and are intended to fall within the appended claims.

For any references that have been cited, the entire disclosures of which are incorporated herein by reference.

What is claimed is:

1. A dentifrice composition comprising an orally acceptable carrier and a cationically modified silica in an amount effective to treat or prevent erosive damage to an enamel surface of a tooth, wherein the cationically modified silica comprises silica covalently bonded to positively charged amino acid, silica covalently bonded to positively charged peptide, or combinations thereof, and wherein the cationically modified silica has a net overall positive charge to enhance residence time of the cationically modified silica on the enamel surface of the tooth.

2. The composition of claim 1, wherein positively charged amino acid is lysine.

3. The composition of claim 1, wherein the positively charged peptide is polylysine.

4. The composition of claim 1, wherein the amount of cationically modified silica effective to treat or prevent erosive damage to an enamel surface of a tooth is 0.01 wt. % to 30 wt. % based on the weight of the composition.

5. The composition of claim 1, wherein the amount of cationically modified silica effective to treat or prevent erosive damage to an enamel surface of a tooth is 0.05 wt. % to 20 wt. % based on the weight of the composition.

6. The composition of claim 1, wherein the amount of cationically modified silica effective to treat or prevent erosive damage to an enamel surface of a tooth is 0.1 wt. % to 10 wt. % based on the weight of the composition.

7. The composition of claim 1, wherein the amount of cationically modified silica effective to treat or prevent erosive damage to an enamel surface of a tooth is 1 wt. % to 5 wt. % based on the weight of the composition.

8. The composition of claim 1 further comprising an abrasive, binder, surfactant, humectant, source of fluoride, and combinations thereof.

9. The composition of claim 1, wherein the composition is a toothpaste.

10. A method of treating or preventing erosive damage to an enamel surface of a tooth comprising administering to a subject in need thereof a dentifrice composition comprising an orally acceptable carrier and an effective amount of a cationically modified silica, wherein the cationically modified silica comprises silica covalently bonded to positively charged amino acid, silica covalently bonded to positively charged peptide, or combinations thereof, and wherein the cationically modified silica has a net overall positive charge to enhance residence time of the cationically modified silica on the enamel surface of the tooth.

11. The method of claim 10, wherein the subject is a mammal.

12. The method of claim 10, wherein the subject is a human.

13. The method of claim 10, wherein the subject is a companion animal.

14. The method of claim 10, wherein the effective amount is 0.01 wt. % to 30 wt. % based on the weight of the composition.

15. The method of claim 10, wherein the effective amount is 0.05 wt. % to 20 wt. % based on the weight of the composition.

16. The method of claim 10, wherein the effective amount is 0.1 wt. % to 10 wt, % based on the weight of the composition.

17. The method of claim 10, wherein the effective amount is 1 wt. % to 5 wt. % based on the weight of the composition.

18. The method of claim 10, wherein the composition further comprises an abrasive, binder, surfactant, humectant, source of fluoride, and combinations thereof.

19. The method of claim 10, wherein the composition is a toothpaste.

20. The composition of claim 4, wherein the positively charged amino acid is lysine and the positively charged peptide is polylysine.

21. The composition of claim 20, wherein the amount of cationically modified silica effective to treat or prevent erosive damage to an enamel surface of a tooth is 1 wt. % to 5 wt. % based on the weight of the composition.

22. The composition of claim 21, wherein the composition is a toothpaste.

23. The method of claim 10, wherein the positively charged amino acid is lysine and the positively charged peptide is polylysine.

* * * * *